(12) United States Patent
Kitano

(10) Patent No.: US 10,512,390 B2
(45) Date of Patent: Dec. 24, 2019

(54) ENDOSCOPE WITH CABLE LINK STRUCTURE

(71) Applicant: FUJIFILM Corporation, Tokyo (JP)

(72) Inventor: Ryou Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 689 days.

(21) Appl. No.: 15/002,402

(22) Filed: Jan. 21, 2016

(65) Prior Publication Data

US 2016/0213229 A1 Jul. 28, 2016

(30) Foreign Application Priority Data

Jan. 26, 2015 (JP) ................. 2015-012554
Jul. 3, 2015 (JP) ................. 2015-134617

(51) Int. Cl.
*A61B 1/00* (2006.01)
*H04N 5/225* (2006.01)

(52) U.S. Cl.
CPC ........ *A61B 1/00096* (2013.01); *A61B 1/0011* (2013.01); *A61B 1/00112* (2013.01);
(Continued)

(58) Field of Classification Search
CPC ............. A61B 1/00096; A61B 1/0011; A61B 1/00124; A61B 1/051; A61B 1/04;
(Continued)

(56) References Cited

U.S. PATENT DOCUMENTS 8,956,279 B2 2/2015 Kitano
2008/0204863 A1* 8/2008 Vogeli ............... A61B 1/00188
359/363

(Continued)

FOREIGN PATENT DOCUMENTS

JP 2010069186 4/2010
JP 2012157472 8/2012
(Continued)

OTHER PUBLICATIONS

"Office Action of China Counterpart Application" dated Jul. 4, 2018, with English translation thereof, p. 1-p. 15.
(Continued)

*Primary Examiner* — Timothy J Neal
*Assistant Examiner* — William B Chou
(74) *Attorney, Agent, or Firm* — JCIPRNET

(57) ABSTRACT

An endoscope includes: a shooting lens unit having a shooting lens and a housing which holds the shooting lens; a prism on which shooting light coming from the shooting lens shines; a prism holding structure which holds the prism and is attached to one end portion of the housing; an image area sensor which is attached to an exit face of the prism; a circuit board which drives the image area sensor; a transmission cable which is electrically connected to the circuit board; and a cable link structure one end portion of which is fastened to the transmission cable and other end portion of which is attached to a body structure having the prism holding structure and the housing, and the other end portion of the cable link structure is formed with a lock portion as defined herein.

12 Claims, 13 Drawing Sheets

(52) U.S. Cl.
CPC ....... *A61B 1/00124* (2013.01); *A61B 1/00114* (2013.01); *A61B 1/00117* (2013.01); *A61B 1/00119* (2013.01); *A61B 1/00121* (2013.01); *H04N 2005/2255* (2013.01)

(58) Field of Classification Search
CPC ............ A61B 1/00112; A61B 1/00114; A61B 1/00117; A61B 1/00119; A61B 1/00121; G02B 7/18; G02B 23/243; G02B 23/2484; G02B 23/24
USPC .................................................. 600/132, 175
See application file for complete search history.

(56) References Cited

U.S. PATENT DOCUMENTS

| | | |
|---|---|---|
| 2012/0197081 A1 | 8/2012 | Kimura |
| 2013/0085328 A1 | 4/2013 | Kitano |

FOREIGN PATENT DOCUMENTS

| | | |
|---|---|---|
| JP | 2012205807 | 10/2012 |
| JP | 2013-075026 | 4/2013 |
| JP | 2013075029 | 4/2013 |

OTHER PUBLICATIONS

"Office Action of Japan Counterpart Application," with machine English translation thereof, dated Feb. 6, 2018, p. 1-p. 9, in which the listed references were cited.

\* cited by examiner

ENDOSCOPE WITH CABLE LINK STRUCTURE

CROSS-REFERENCE TO RELATED APPLICATIONS

This application claims the benefit of Japanese Patent Application JP 2015-012554, filed Jan. 26, 2015, and Japanese Patent Application JP 2015-134617, filed Jul. 3, 2015, the entire contents of which are hereby incorporated by reference, the same as if set forth at length.

FIELD OF THE INVENTION

The present invention relates to an endoscope.

BACKGROUND OF THE INVENTION

Endoscopes have an insertion portion to be inserted into, for example, the body cavity of a subject body. The insertion portion is composed of a tip hard portion, a curved portion, and a soft portion which are arranged in this order from the tip. The tip surface of the tip hard portion is provided with an observation window, illumination windows, a forceps outlet, and an air/water supply nozzle. A camera module and light guides are attached to the inner wall of the tip hard portion at such positions as to correspond to the observation window and the illumination window, respectively. The curved portion is formed by connecting plural joint ring units and can thereby direct the tip hard portion to a desired direction by a wire manipulation. The soft portion has a length of 1 to 2 m to allow the tip hard portion to reach a desired observation part of a subject body.

The camera module is composed of a shooting lens unit and an imaging unit. The shooting lens unit is configured in such a manner that plural lenses are housed in a housing. The imaging unit is equipped with an image area sensor such as a CCD (charge-coupled device) or a CMOS (complementary metal-oxide-semiconductor) sensor for photoelectrically converting an optical image formed by the shooting lens unit into an image signal. The image area sensor is connected to a transmission cable via a circuit board such as a flexible board or a sub-board. The flexible board or sub-board is mounted with electronic components for driving the image area sensor. An output signal of the imaging unit is sent, via the flexible board or sub-board and the transmission cable, to an image processing device, which performs image processing on the received signal and displays an image of, for example, a lesion on the monitor.

The transmission cable which sends a signal from the imaging unit to the image processing device is a composite multicore cable. Inserted in the insertion portion over its entire length, the transmission cable is pushed and pulled strongly every time the insertion portion is looped or bent. When the transmission cable is pulled in, a problem may occur that peeling occurs at the connection portion of the transmission cable and the circuit board or the transmission cable is disconnected.

To avoid such a disconnection or peeling, in the endoscope disclosed in JP-A-2013-75026, a cable link structure is disposed in an empty space between the inner circumferential wall of a tip hard portion and an image area sensor. The cable link structure is disposed close to the image area sensor approximately parallel with it. One end portion of the cable link structure is fastened to the outer sheath of the transmission cable and the other end portion is attached to a fixing cylinder of a prism holding structure that is part of the tip hard portion. The other end portion of the cable link structure is formed with a lock nail to lock on the attachment cylinder of the prism holding structure. Therefore, even if the insertion portion of the endoscope is bent repeatedly and the transmission cable is pulled each time, since a pull is transmitted to the prism holding structure via the cable link structure, no pull acts on the circuit board etc., thus preventing peeling at the connection portion of the transmission cable and the circuit board and a disconnection of the transmission cable.

SUMMARY OF THE INVENTION

In the endoscope disclosed in JP-A-2013-75026, the cable link structure is fastened to the attachment cylinder of the prism holding structure with the lock nail (provided at the other end of the cable link structure) locked on the tip surface of the attachment cylinder. However, the cable link structure is made of a thin metal plate and the lock nail formed by bending a tip portion of the metal plate by 90° is locked on the tip surface of the attachment cylinder. Therefore, if force acts on the cable link structure in a direction in which its flexural strength is low, the lock nail, and hence the cable link structure, disengages from the attachment cylinder The present invention has been made in view of the above circumstances, and an object of the invention is therefore to provide an endoscope in which the connection strength of the cable link structure against a pull transmitted by the transmission cable can be increased.

An endoscope according to an aspect of the invention comprises: a shooting lens unit having a shooting lens and a housing which holds the shooting lens; a prism on which shooting light coming from the shooting lens shines; a prism holding structure which holds the prism and is attached to one end portion of the housing; an image area sensor which is attached to an exit face of the prism; a circuit board which drives the image area sensor; a transmission cable which is electrically connected to the circuit board; and a cable link structure one end portion of which is fastened to the transmission cable and the other end portion of which is attached to a body structure having the prism holding structure and the housing, wherein: the other end portion of the cable link structure is formed with a lock portion which is locked on the body structure; and the lock portion restricts movement of the cable link structure relative to the body portion in two different directions.

The invention can provide an endoscope in which the connection strength of the cable link structure against a pull transmitted by the transmission cable can be increased.

DESCRIPTION OF SYMBOLS

Figure 1:
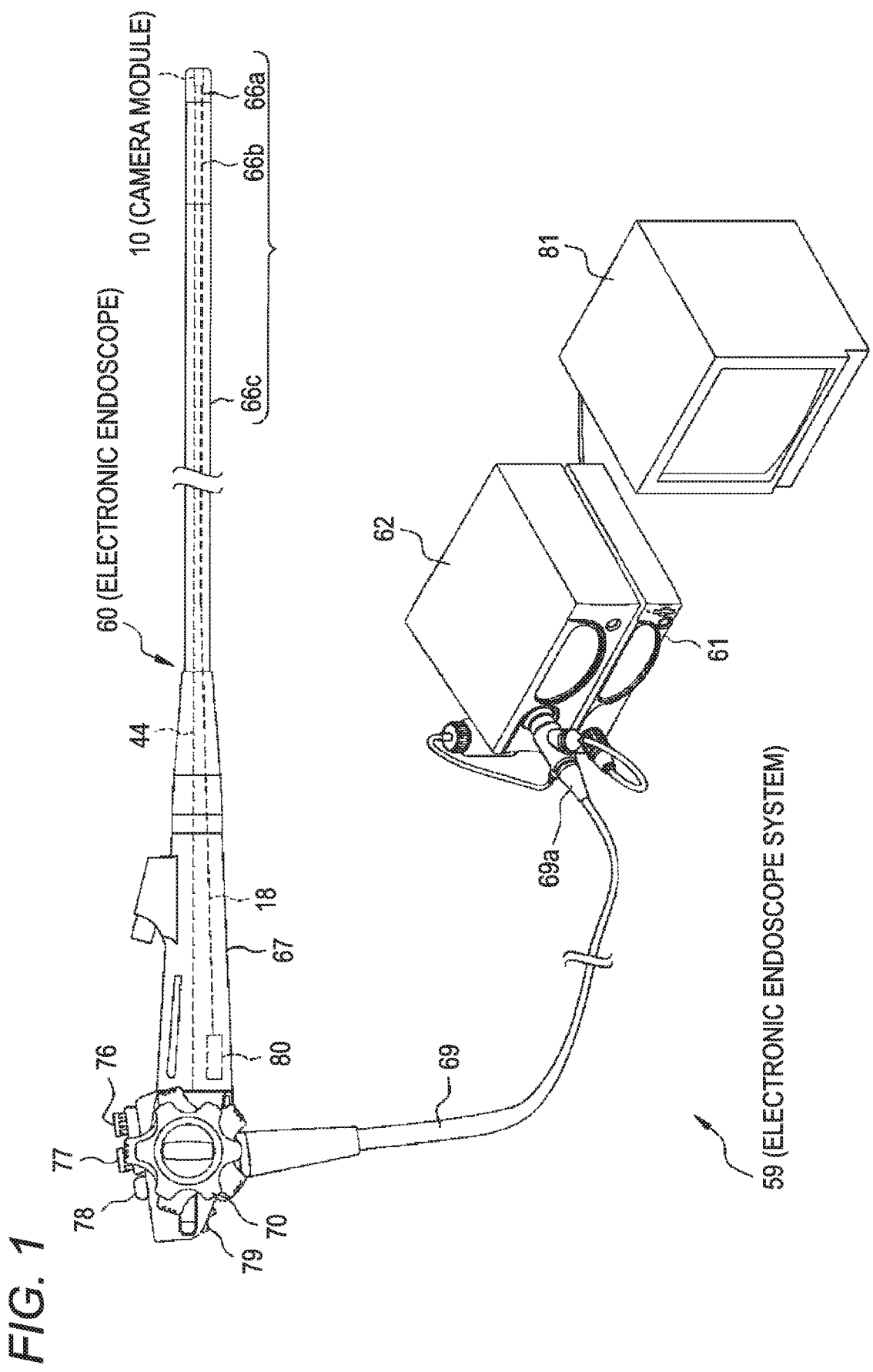
FIG. 1 is a perspective view showing the configuration of an electronic endoscope system according to each embodiment of the present invention.

10: Camera module
11: Shooting lens unit
12: Imaging unit
13: Housing
14: Shooting lens
40: Prism holding structure
40c: Cut
41: Prism
42: Image area sensor
43: Circuit board
44: Transmission cable
44a: Wire
44b: Shield line
44c: Outer sheath
45, 55: Cable link structure
47: Lock nail
53: Nail
54: Cut
57: Arm
58, 68: Link portion
59: Electronic endoscope system
60: Endoscope

DETAILED DESCRIPTION OF THE INVENTION

Embodiments of the present invention will be hereinafter described with reference to the drawings.

FIG. 1 is a perspective view showing the configuration of an electronic endoscope system 59 according to a first embodiment of the invention. As shown in FIG. 1, the electronic endoscope system 59 is equipped with an electronic endoscope (hereinafter referred to simply as an "endoscope") 60, a light source apparatus 62, a processor apparatus 61, and a monitor 81.

(Endoscope)

The endoscope 60 is equipped with a flexible insertion portion 66 to be inserted into, for example, the body cavity of a subject body, a hand manipulation unit 67 which is continuous with a proximal portion of the insertion portion 66, a connector 69a which is connected to the processor apparatus 61 and the light source apparatus 62, and a universal cord 69 which connects the hand manipulation unit 67 to the connector 69a.

Figure 2:
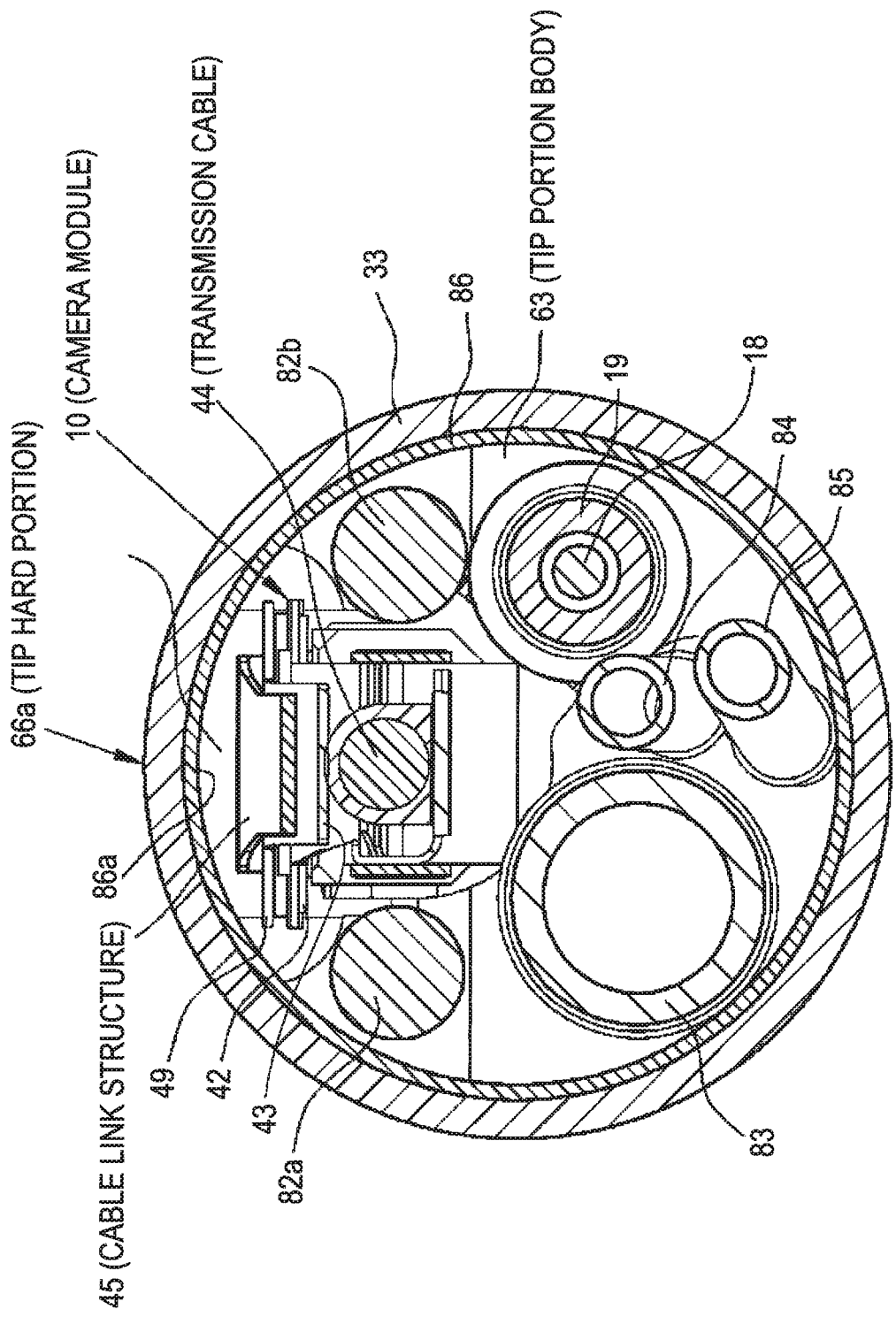
FIG. 2 is a sectional view of a tip hard portion of an endoscope according to a first embodiment of the invention.

The insertion portion 66 is composed of a tip hard portion 66a, a curved portion 66b, and a soft portion 66c which are arranged in this order from the tip. FIG. 2 shows a sectional shape of the tip hard portion 66a. As shown in FIG. 2, the tip hard portion 66a is configured in such a manner that a hard resin tip portion body 63 is covered with a soft resin tip cap and the tip portion body 63 and a metal tip cylinder 86, adjacent to the tip portion body 63, of the curved portion 66b are covered with a tube. As shown in FIG. 1, a camera module 10 is attached to the tip hard portion 66a inside.

In addition to the camera module 10, light guides 82a and 82b, a forceps channel 83, an air supply tube 84, and a water supply tube 85 are attached to the tip portion body 63 inside. The camera module 10 is fixed to the tip portion body 63 as a result of a housing 13's being inserted into a fixing hole formed through the tip portion body 63 and screwed to it. An image area sensor 42 of the camera module 10 is disposed close to the inner circumferential surface of the tip portion body 63, more correctly, the inner circumferential surface of the tip cylinder 86 of the curved portion 66b.

In the circular tip cylinder 86, since image area sensor 42 is disposed near it, a gap is formed between the image area sensor 42 and the inner circumferential surface 86a of the tip cylinder 86 and forms a dead space 87. In the embodiment, a cable link structure 45 is disposed in the dead space 87.

Having joint ring units that are pin-connected to each other, the curved portion 66b is curved in its entirety. The curved portion 66b is curved at any angle in each of the top, bottom, left, and right directions by rotating an angle knob 70 of the hand manipulation unit 67. As a result, an observation part in a body cavity can be shot by the camera module 10 by setting the tip hard portion 66a in a desired direction in the body cavity.

The soft portion 66c is a long, narrow-diameter portion that is flexible and connects the curved portion 66b to the hand manipulation unit 67.

Figure 3:
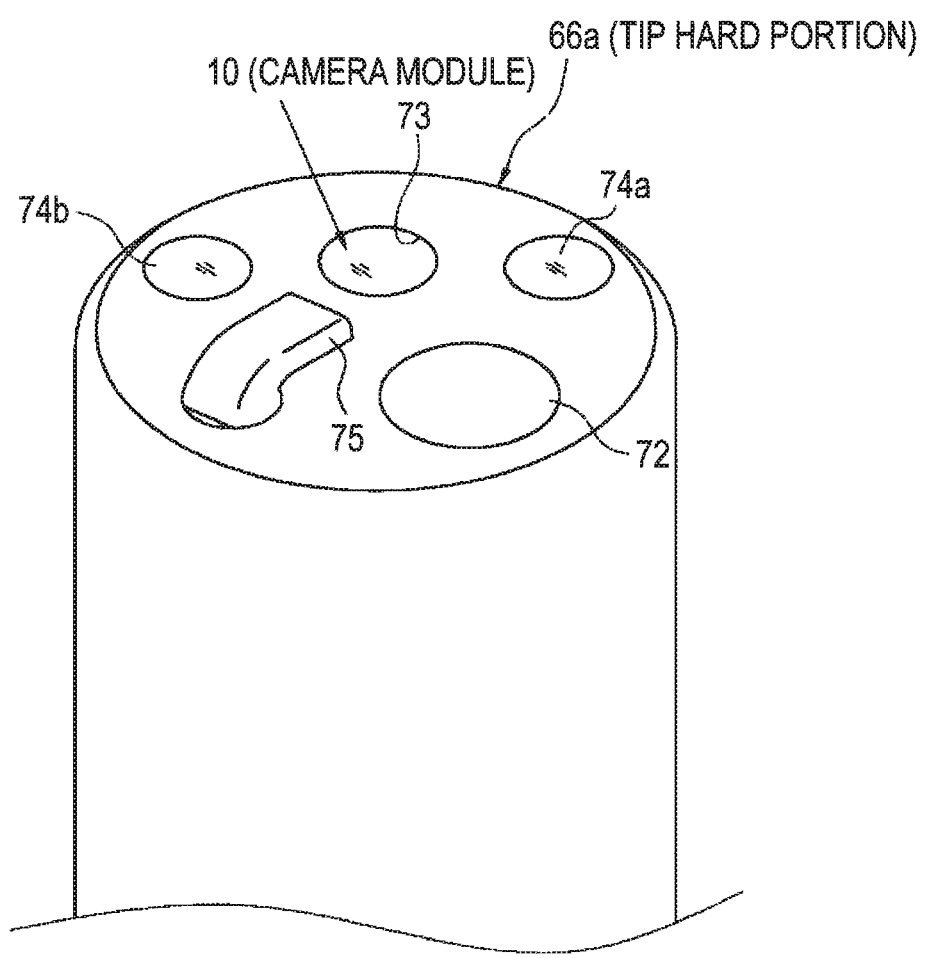
FIG. 3 is a perspective view of the tip hard portion.

As shown in FIG. 3, the tip surface of the tip hard portion 66a is formed with a forceps outlet 72, an observation window 73, illumination windows 74a and 74b, and an air/water supply nozzle 75. A lens of the camera module 10 is disposed in the observation window 73, the light guides 82a and 82b are connected to the respective illumination windows 74a and 74b, and the air supply tube 84 and the water supply tube 85 are connected to the air/water supply nozzle 75.

The hand manipulation unit 67 is equipped with various manipulation members such as the angle knob 70, an air/water supply button 76, a suction button 77, a release button 78, and a seesaw switch 79 for zoom manipulation. The angle knob 70 is used to direct the tip hard portion 66a of the insertion portion 66 in any of the top, bottom, left, and right directions by rotating it. The air/water supply button 76 is used to cause air or water to be ejected from the air/water supply nozzle 75 by pushing it. The suction button 77 is used to suck an object to be sucked such as liquid, tissue, or the like existing in a subject body through the forceps outlet 72 by pushing it. The release button 78 is used to record an observation image in the form of a still image by means of the camera module 10 by pushing it. The seesaw switch 79 is used to switch the shooting mode of the shooting lens between standard shooting and enlargement shooting by causing a motor 80 to rotate in the normal or reverse direction and having the rotation transmitted to a cam shaft via a wire 18.

(Light Source Apparatus)

The light source apparatus 62 supplies the endoscope 60 with illumination light for illuminating an observation part in a body cavity through the illumination windows 74a and 74b which are formed in the tip surface of the tip hard portion 66a. Illumination light that is supplied from the light source apparatus 62 is transmitted to the tip surface of the tip hard portion 66a by the universal cord 69 of the endoscope 60 and its light guides 82a and 82b each of which is a bundle of a large number of optical fibers and is inserted in the insertion portion 66.

(Processor Apparatus)

The processor apparatus 61 is electrically connected to the light source apparatus 62 and supervises operations of the electronic endoscope system 59. The processor apparatus 61 supplies power to the endoscope 60 via the universal cord 69 and the transmission cable 44 which is inserted in the insertion portion 66, and controls driving of the camera module 10 provided in the tip hard portion 66a. Furthermore, the processor apparatus 61 receives a signal from the camera module 10 via the transmission cable 44 and generates image data by performing various kinds of processing on it.

(Monitor)

Connected to the processor apparatus 61, the monitor 81 displays an observation image on the basis of image data that is supplied from the processor apparatus 61.

Figure 4:
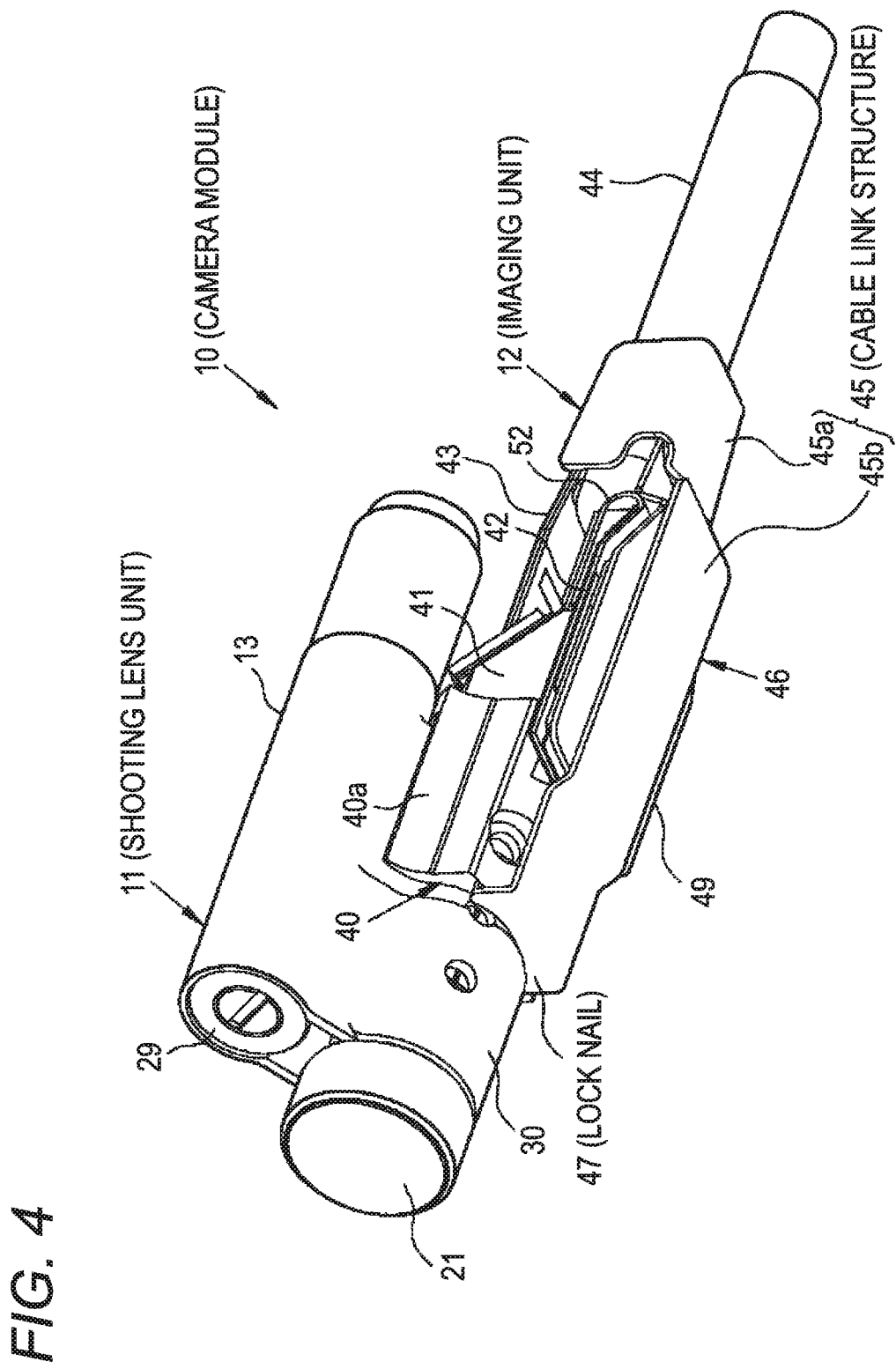
FIG. 4 is a perspective view showing an overall appearance of a camera module of the endoscope according to the first embodiment.
Figure 5:
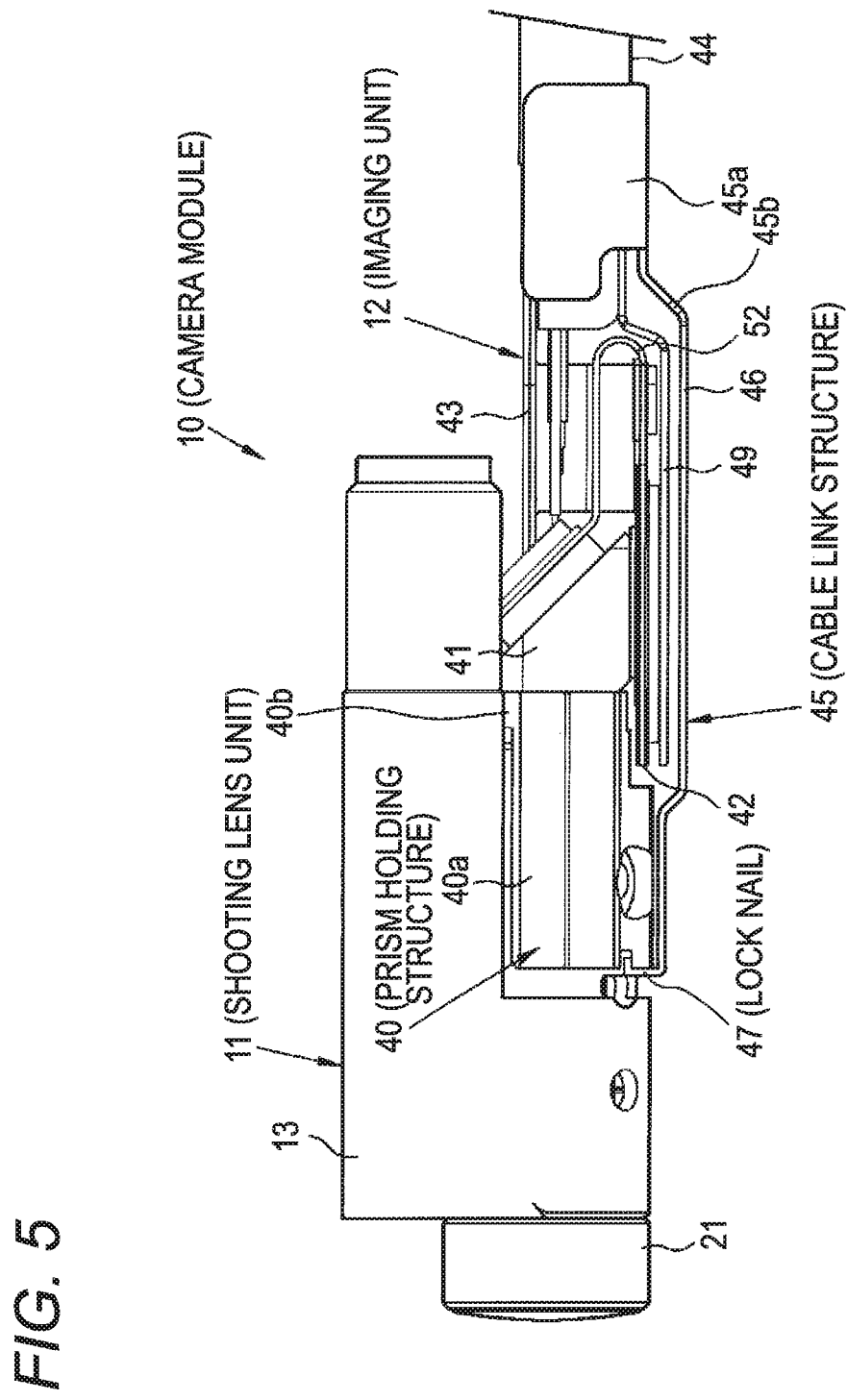
FIG. 5 is a side view showing an overall appearance of the camera module.

Next, a description will be made of the camera module 10 which is provided in the tip hard portion 66a of the insertion portion 66 of the endoscope 60. As shown in FIGS. 4 and 5, the camera module 10 is equipped with a shooting lens unit 11 and an imaging unit 12, each of which will be described below in detail.

(Shooting Lens Unit)

Figure 6:
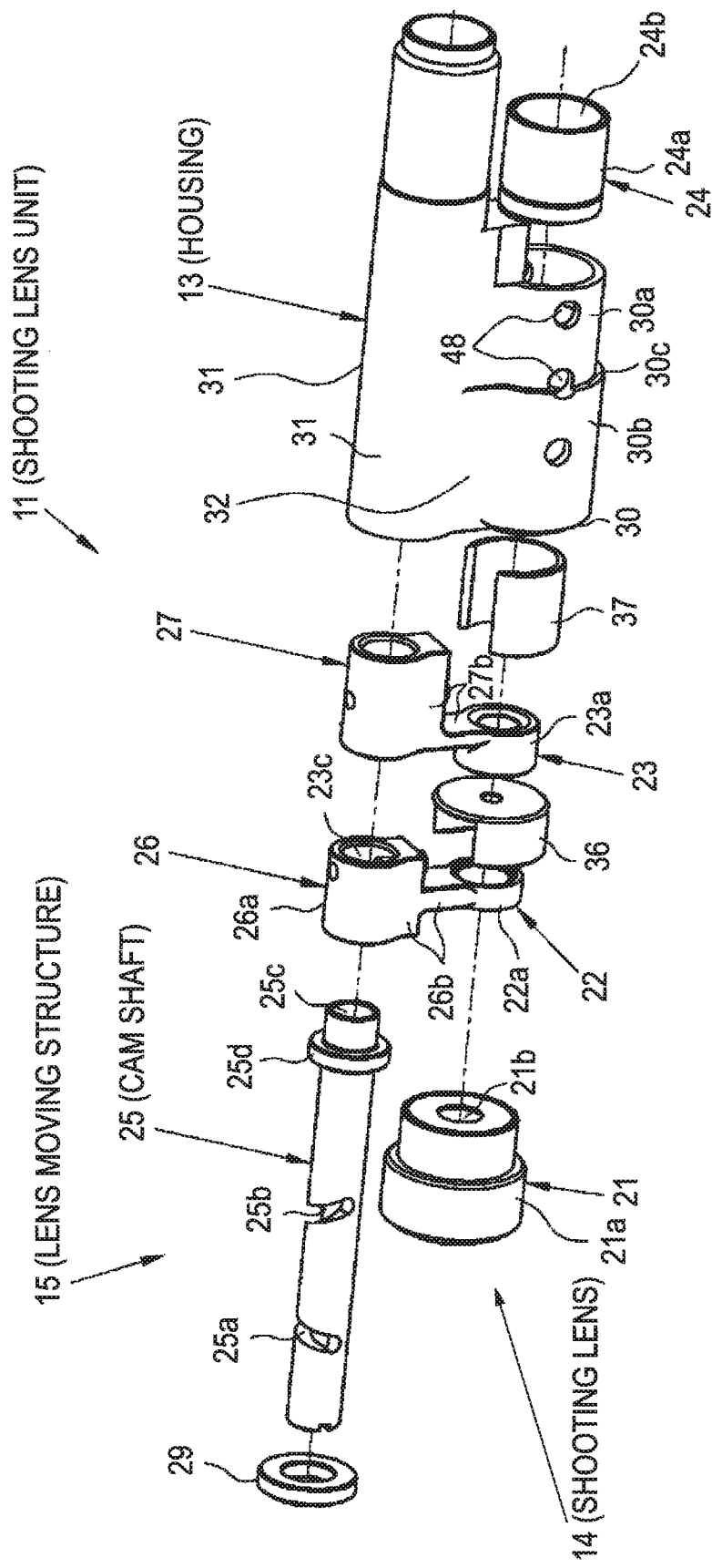
FIG. 6 is an exploded perspective view of a shooting lens unit of the endoscope according to the first embodiment.
Figure 7:
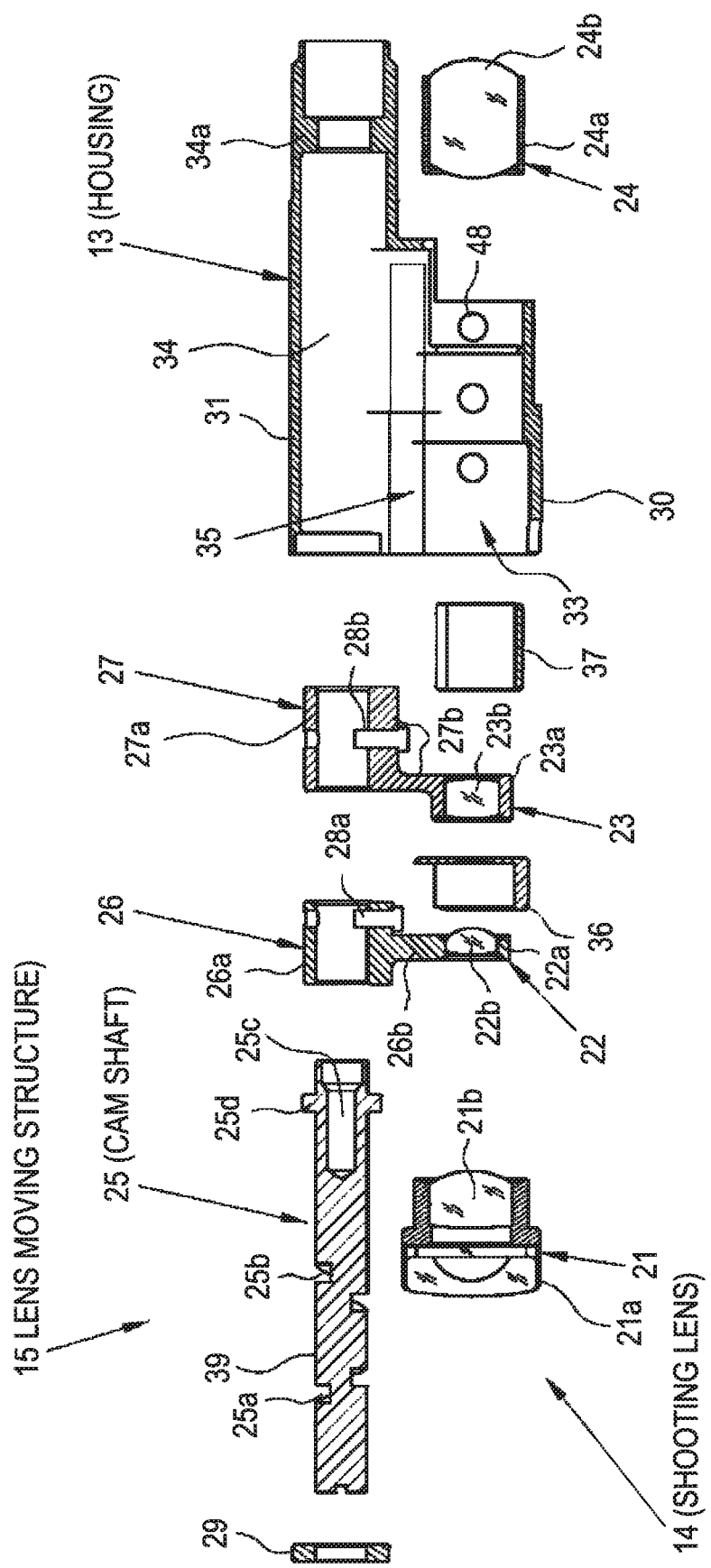
FIG. 7 is an exploded side view of the shooting lens unit.

As shown in FIGS. 6 and 7, the shooting lens unit 11 is equipped with a housing 13 and a shooting lens 14 and a lens moving structure 15 which are housed in the housing 13.

The shooting lens 14 is composed of a first fixed lens 21, a first movable lens 22, a second movable lens 23, and a second fixed lens 24 which are arranged in this order in the optical axis direction. The lenses 21-24 are composed of lens frames 21a-24a and a single or plural lens bodies 21b-24b (each being a single or plural lenses) which are held by the respective lens frames 21a-24a.

The lens moving structure 15 has a cam shaft 25, a first lens moving frame 26 and a second lens moving frame 27 which slide on the cam shaft 25. The lens moving structure 15 enables variable magnification shooting by varying the focal length of the shooting lens 14 by moving the first movable lens 22 and the second movable lens 23 in the optical axis direction.

Figure 8:
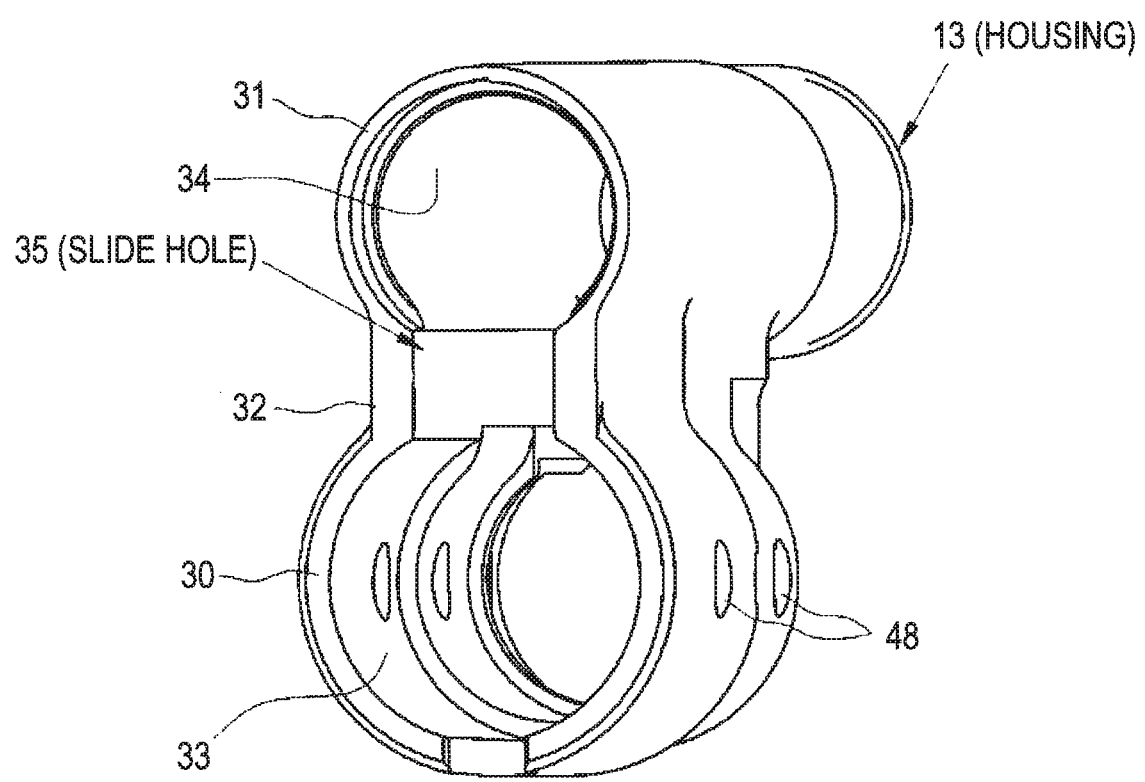
FIG. 8 is a perspective view of a housing, as viewed obliquely from the front side, of the endoscope according to the first embodiment.

As shown in FIG. 8, the housing 13 is configured in such a manner that a first cylinder 30 and a second cylinder 31 are arranged in the direction perpendicular to the cylinder axis direction and connected to each other by a connection portion 32. The second cylinder 31 is a little smaller in outer diameter than the first cylinder 30, and the housing 13 is shaped like a figure "8" when viewed from the front side. The first cylinder 30 has a shooting lens housing hole 33 for housing of the shooting lens 14. The second cylinder 31 has a lens moving structure housing hole 34 for housing of the lens moving structure 15.

As shown in FIG. 7, a lock ring 34a projects in the lens moving structure housing hole 34. A slide hole 35 that connects the shooting lens housing hole 33 and the lens moving structure housing hole 34 is formed in the connection portion 32. Holes 48 that are formed through the wall of the first cylinder 30 are for injection of adhesive or insertion of screws in fixing antireflection cylinders 36 and 37 and the second fixed lens 24 to the first cylinder 30 and setting them in the shooting lens housing hole 33. The holes 48 are formed if necessary.

As shown in FIGS. 6 and 7, the cam shaft 25 is formed with two cam grooves, that is, a first cam groove 25a and a second cam groove 25b. A wire link hole 25c is formed through a rear end portion of the cam shaft 25 along its axis, and a lock flange 25d projects from a portion, close to its rear end, of the outer circumferential surface of the cam shaft 25. The tip of the wire 18 for rotational driving is fixed to the wall of the wire link hole 25c. The wire 18 is inserted in a protective tube 19 and linked to the motor 80 (see FIG. 1) which is provided in the hand manipulation unit 67. The motor 80 is drive-controlled by a controller (not shown) so as to be rotated in the normal or reverse direction according to a manipulation on the seesaw switch 79 of the hand manipulation unit 67.

As shown in FIGS. 6 and 7, a fixing ring 29 is attached to the front end of the cam shaft 25. Because of the presence of the fixing ring 29, the cam shaft 25 rotates smoothly in the lens moving structure housing hole 34 without inclining. Since the rear-end lock flange 25d of the cam shaft 25 is locked on the lock ring 34a, the cam shaft 25 does not come off the lens moving structure housing hole 34.

As shown in FIGS. 6 and 7, the first lens moving frame 26 has a guide cylinder 26a, a lens frame 22a, and an arm 26b which links them. The guide cylinder 26a, the lens frame 22a, and the arm 26b constitute an integral member. Likewise, the second lens moving frame 27 has a guide cylinder 27a, a lens frame 23a, and an arm 27b which links them. The guide cylinder 27a, the lens frame 23a, and the arm 26b constitute an integral member. A first engagement pin 28a is attached to the guide cylinder 26a of the first lens moving frame 26, and the tip of the first engagement pin 28a is set inside the first cam groove 25a. A second engagement pin 28b is attached to the guide cylinder 27a of the second lens moving frame 27, and the tip of the second engagement pin 28b is set inside the second cam groove 25b.

When the cam shaft 25 is rotated in the normal or reverse direction by the motor 80 (see FIG. 1), the cam shaft 25 is displaced in the rotational direction, whereby the first lens moving frame 26 and the second lens moving frame 27 are moved via the first engagement pin 28a and the second engagement pin 28b, respectively, in the optical axis direction in the housing 13.

Figure 9:
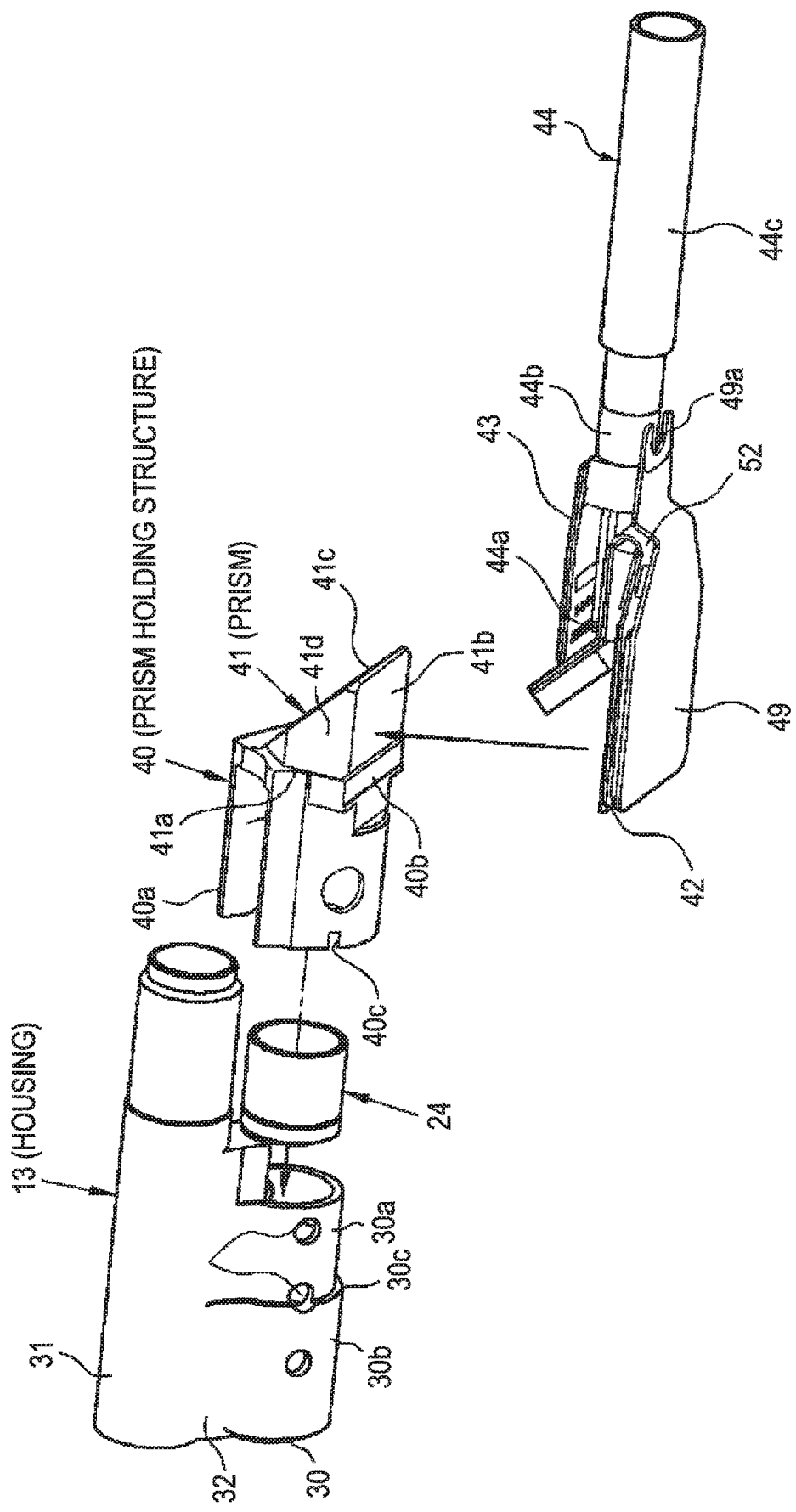
FIG. 9 is a perspective view showing the housing, a prism holding member, and electric components such as an image area sensor in an exploded manner.

As shown in FIGS. 6 and 9, a rear half 30a of the outer circumferential surface of the first cylinder 30 of the housing 13 is slightly smaller in diameter than its front half 30b, as a result of which a step surface 30c is formed between the front half 30b and the rear half 30a. A prism holding structure 40 of the imaging unit 12 is attached to the rear half 30a of the outer circumferential surface.

(Imaging Unit)

As shown in FIGS. 4 and 5, the imaging unit 12 is equipped with the prism holding structure 40, a prism 41, the image area sensor 42, a circuit board 43, the transmission cable 44, the cable link structure 45, a heat radiation plate 49, and a sealing agent (not shown) for sealing of wires.

As shown in FIG. 9, the prism holding structure 40 has an attachment cylinder 40a which is attached to a rear end portion of the first cylinder 30 of the housing 13 and a prism attachment frame 40b to which the prism 41 is attached. A front end portion of the attachment cylinder 40a is formed with cuts 40c which are fitted with respective portions of the lock nail 47 of the cable link structure 45 (described later), respectively. The cuts 40c are formed so as to extend in the direction from the front end of the attachment cylinder 40a to the prism attachment frame 40b.

The prism 41 is a rectangular prism having five faces, that is, an incident face 41a and an exit face 41b which are perpendicular to each other, a reflection face 41c which is a slant face, and two side faces 41d.

As shown in FIGS. 4, 5, and 9, the image area sensor 42 is attached to the exit face 41b of the prism 41 and the circuit board 43 for driving the image area sensor 42 is attached to the reflection face 41c of the prism 41 with adhesive. The circuit board 43 is connected to the image area sensor 42 via a flexible wiring board 52, wires (not shown), etc. Wires (signal wires) 44a of the transmission cable 44 are electrically connected to the circuit board 43. As shown in FIG. 9, the transmission cable 44 is composed of the plural wires 44a, a shield line 44b which bundles and shields them, and an outer sheath 44c which covers the shield line 44b. The circuit board 43 may have plural sub-boards in addition to a main board.

The heat radiation plate 49 is fastened to the image area sensor 42 from outside. A rear end portion of the heat radiation plate 49 is formed with a cable receiving portion 49a, which is soldered to the shield line 44b of the transmission cable 44. The heat radiation plate 49 allows heat to escape from the image area sensor 42 to the transmission cable 44.

Figure 10:
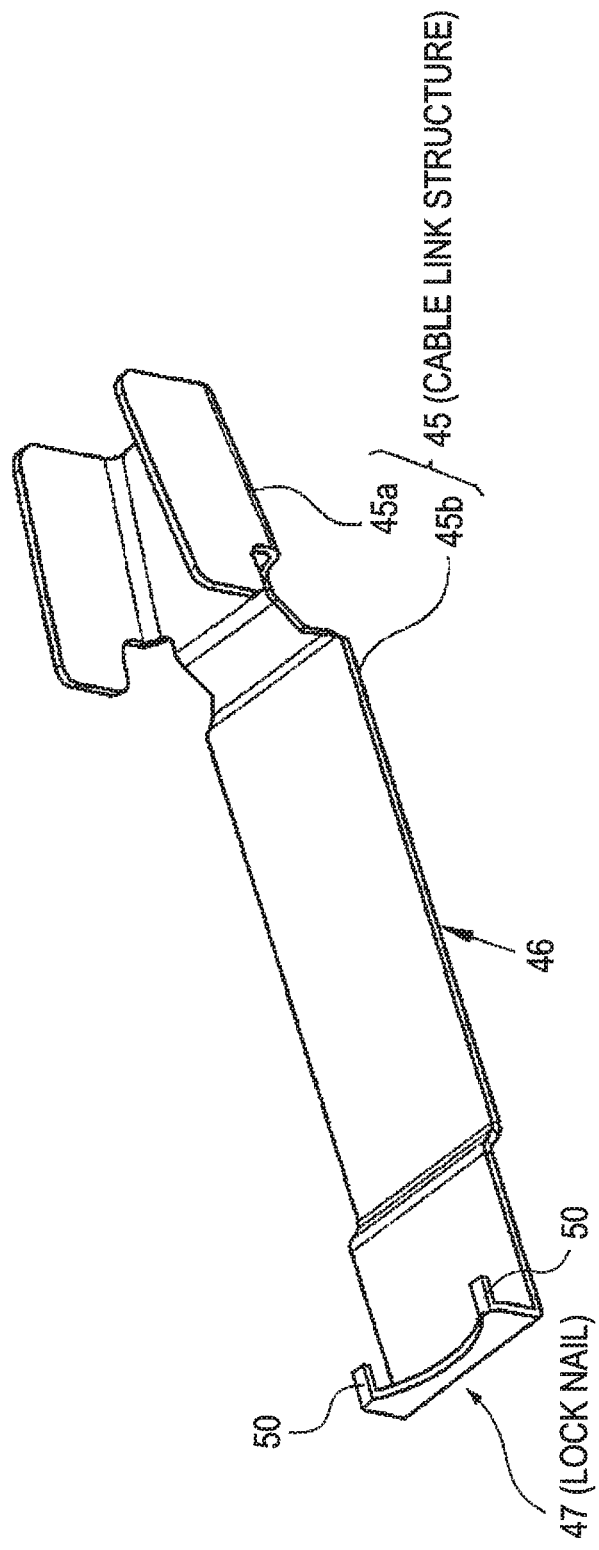
FIG. 10 is a perspective view of a cable link member of the endoscope according to the first embodiment.

One end portion of the cable link structure 45 which is made of an approximately T-shaped metal plate is fastened to the outer sheath 44c of the transmission cable 44 with adhesive on the same side as the cable receiving portion 49a of the heat radiation plate 49 is soldered. As shown in FIG. 10, the cable link structure 45 is composed of an attachment frame portion 45a which is formed by bending both side portions, located at the one end, of a T-shaped metal plate and a link plate portion 45b which is formed at the other end of the T-shaped metal plate.

The attachment frame portion 45a which is one end portion of the cable link structure 45 is U-shaped in cross section. As shown in FIGS. 4 and 5, the attachment frame portion 45a is disposed so as to surround the transmission cable 44 and the one end portion of the cable link structure 45 is fastened to the outer sheath 44c of the transmission cable 44 by charging adhesive into the gap between the attachment frame portion 45a and the transmission cable 44.

The link plate portion 45b has the lock nail 47 which is located at the other end of the cable link structure 45 and an offset portion 46 which is a central portion of the cable link structure 45. The other end portion of the cable link structure 45 is approximately U-shaped. The lock nail 47 is composed of a first lock portion which is formed by bending the other end portion of the cable link structure 45 by 90° and second lock portions which are formed by bending two projections 50 of the other end portion of the cable link structure 45 by 900 toward the side of the offset portion 46. The top edge of a front flange, located between the two projections 50, of the lock nail 47 is arc-shaped so as to conform to the outer circumferential surface of the first cylinder 30 of the housing 13.

As shown in FIGS. 4 and 5, the lock nail 47 is in contact with the front end surface of the attachment cylinder 40a of the prism holding structure 40 and the two projections 50 of the lock nail 47 are fitted in the respective cuts 40c which are formed in the front end portion of the attachment cylinder 40a, whereby the cable link structure 45 is locked on the front end portion of the attachment cylinder 40a. The top surface of the portion, between the lock nail 47 and the offset portion 46, of the cable link structure 45 is a surface to be bonded to the attachment cylinder 40a, and the other end portion of the cable link structure 45 is fastened to the attachment cylinder 40a of the prism holding structure 40 by charging the gap there with adhesive.

So that the cable link structure 45 being fastened to the prism holding structure 40 does not come into contact with the heat radiation plate 49 which covers the image area sensor 42, the offset portion 46 is offset in such a direction as to go away from the outer circumferential surface of the attachment cylinder 40a according to the positional relationship between the heat radiation plate 49 and the outer circumferential surface of the attachment cylinder 40a of the prism holding structure 40. However, the offset portion 46 is not necessary if the heat radiation plate 49 does not project outward from the level of the outer circumferential surface of the attachment cylinder 40a. In this case, the portion of the cable link structure 45 between the attachment frame portion 45a and the lock nail 47 is shaped like a flat plate.

To protect the wire connection portions, the wires 44a, etc. covered with the cable link structure 45, the image area sensor 42, and the circuit board 43, a sealing agent (not shown) is injected into the gaps there and solidified if necessary.

The offset portion 46 of the cable link structure 45 is shaped like a flat plate so as to cover neither of the two sides of the image area sensor 42. Therefore, even if the image area sensor 42 is changed (i.e., increased) in size, it does not come into contact with the cable link structure 45; the cable link structure 45 can accommodate a size change or the like of the image area sensor 42. Also shaped like a flat plate rather than a frame, the heat radiation plate 49 which protects the image area sensor 42 can likewise accommodate a size change of the image area sensor 42 while maintaining its structure.

As described above, in the above-described embodiment, the imaging unit 12 which is part of the camera module 10 which is provided in the tip hard portion 66a of the insertion portion 66 of the endoscope 60 is equipped with the cable link structure 45 one end portion of which is fastened to the outer sheath 44c of the transmission cable 44 and the other end portion of which is fastened to the attachment cylinder 40a of the prism holding structure 40. Furthermore, the other end portion of the cable link structure 45 is formed with the lock nail 47, which is in contact with the front end surface of the attachment cylinder 40a. And the two projections 50 of the lock nail 47 are fitted in the respective cuts 40c of the front end portion of the attachment cylinder 40a.

Therefore, even in a case that the insertion portion 66 of the endoscope 60 is bent repeatedly and the transmission cable 44 is pulled in two different directions, a pull can be transmitted to the prism holding structure 40 via the cable link structure 45. Since the cable link structure 45 is high in connection strength, no pull acts on the circuit board 43 etc. and hence there do not occur such events as peeling at the connection portion of the transmission cable 44 and the circuit board 43 and a disconnection of the transmission cable 44.

The two projections 50 of the lock nail 47 which are bent toward the side of the offset portion 46 so as to project from the surface, in contact with the attachment cylinder 40a, of the cable link structure 45. The extending direction of the projections 50 is perpendicular to the thickness direction of the cable link structure 45 in which the other end portion of the cable link structure 45 made of a plate-like member is most prone to be displaced by force received at its one end. Therefore, the connection strength of the cable link structure 45 against stress is increased in the direction in which it receives strongest force when warped.

Although in the embodiment the lens moving structure 15 of the shooting lens unit 11 is equipped with the two movable lenses, that is, the first movable lens 22 and the second movable lens 23, the number of movable lenses may be one or more. Instead of a shooting lens unit that is equipped with a movable lens(es) and enables magnification and focus adjustment, a fixed-focus shooting lens unit may be employed.

Although in the embodiment the prism holding structure 40 and the housing 13 are separate structures, they may be integrated together as a body portion of the shooting lens unit 11. Furthermore, although the endoscope 60 according to the embodiment is for medical use, the invention can also be applied to industrial uses.

Figure 11:
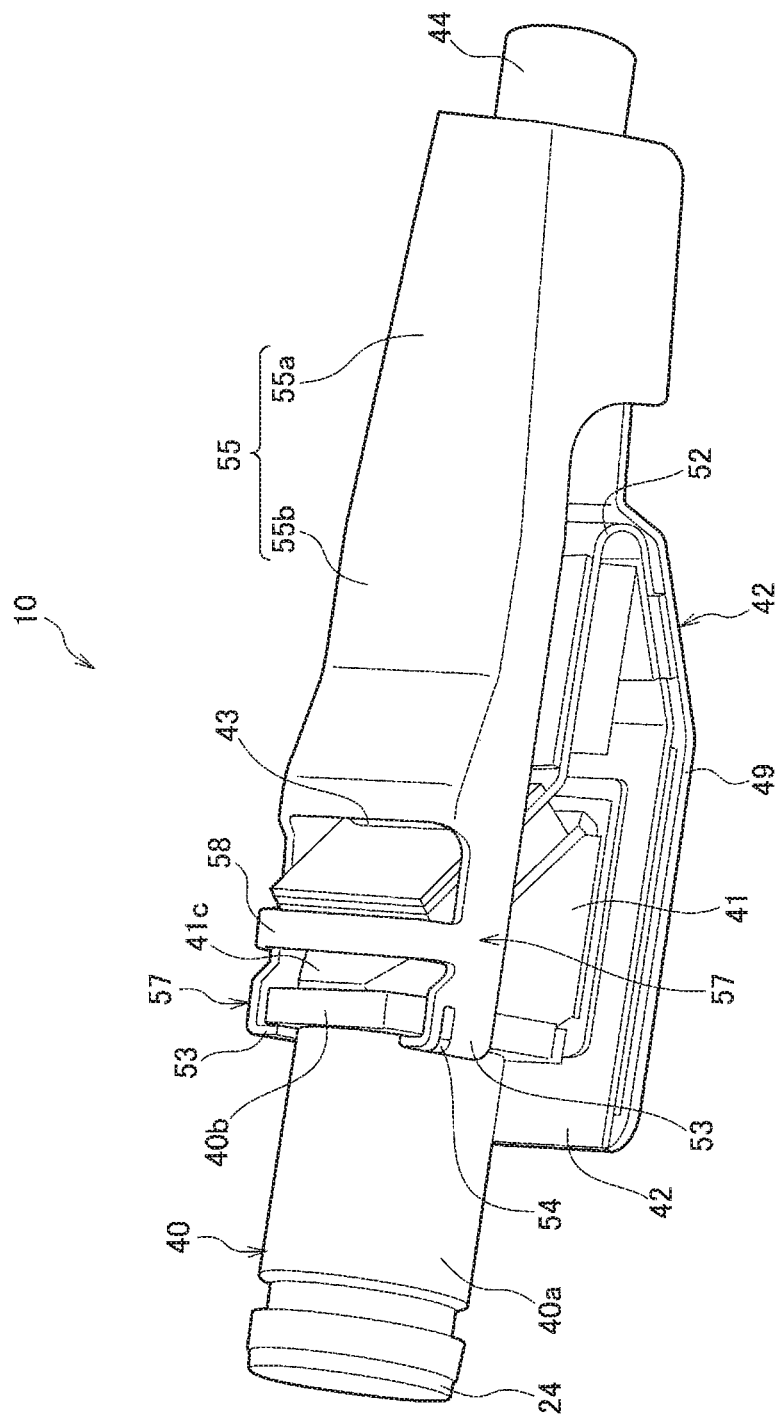
FIG. 11 is a perspective view showing an appearance of a camera module, excluding a housing etc., according to a second embodiment of the invention.
Figure 12:
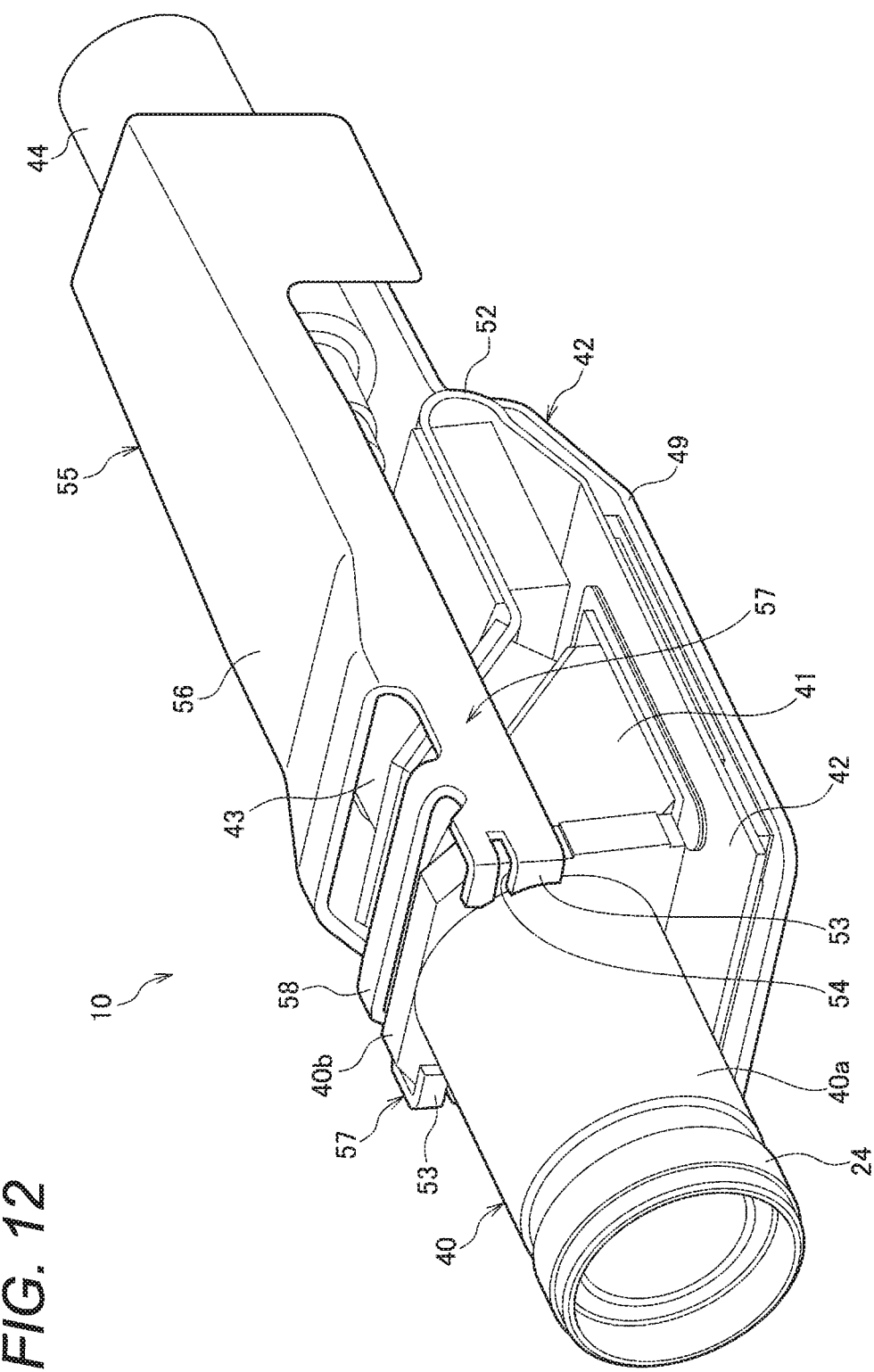
FIG. 12 is a perspective view showing an appearance of the camera module, excluding the housing etc., according to the second embodiment

In the embodiment, as shown in FIG. 2, the cable link structure 45 is disposed in the dead space 87 that is formed between the inner circumferential surface 86a of the tip cylinder 86 and the image area sensor 42. However, as shown in FIGS. 11 and 12, a similar cable link member may be disposed so as to cover the side where the circuit board 43 which is attached to the reflection face 41c of the prism 41 is located. FIGS. 11 and 12 are perspective views showing an appearance of a camera module, excluding the housing 13 etc., according to a second embodiment.

A cable link structure 55 shown in FIGS. 11 and 12 is composed of an attachment frame portion 55a which is formed by bending both side portions, located at one end, of a generally T-shaped and is made of a metal plate so as to have a U-shaped cross section and a link plate portion 55b which is formed at the other end of the T-shaped metal plate.

The attachment frame portion 55a is disposed so as to surround the transmission cable 44 and the one end portion of the cable link structure 55 is fastened to the outer sheath 44c of the transmission cable 44 by charging adhesive into the gap between the attachment frame portion 55a and the transmission cable 44.

The link plate portion 55b has an offset portion 56 which is a central portion of the cable link structure 55, a pair of arms 57 which extend from the offset portion 56 to the other end of the cable link structure 55, and a link portion 58 which links the pair of arms 57. On the other side of the cable link structure 55, each arm 57 is formed with a nail 53, which is locked on the prism attachment frame 40b of the prism holding structure 40. The nail 53 is formed with a cut 54 and is bonded to the prism attachment frame 40b by charging the cut 54 with hard adhesive.

The link portion 58 which links the pair of arms 57 is formed so as to stride over the prism 41. Therefore, the link portion 58 is in contact with or close to the reflection face 41c of the prism 41 and part of the prism 41 is interposed between the link portion 58 and the nails 53. If a gap exists between the link portion 58 and the reflection face 41c of the prism 41 in a state that the cable link structure 55 is attached, the gap is charged with adhesive. Also where gaps exist between the nails 53 and the prism attachment frame 40b, the gaps are charged with adhesive. Since in this manner the part of the prism 41 is sandwiched between the link portion 58 and the nail 53 without forming any gaps, the prism holding structure 40 can hold the prism 41 reliably.

In the above-described second embodiment, the cable link structure 55, which is provided so that no pull acts on the circuit board 43 etc. even if the insertion portion 66 of the endoscope 60 is bent repeatedly and the transmission cable 44 is pulled each time, has the link portion 58 which links the pair of arms 57 which are locked on the prism attachment frame 40b of the prism holding structure 40. When the transmission cable 44 is pulled, the nails 53 of the arms 57 which are formed at the other end of the cable link structure 55 receive forces that are in such directions (which are different from the direction of the pull) as to cause the nails to go away from each other. However, the link portion 58 can oppose those forces. Thus, the strength of the connection between the cable link structure 55 and the prism holding structure 40 against a pull transmitted by the transmission cable 44.

Figure 13:
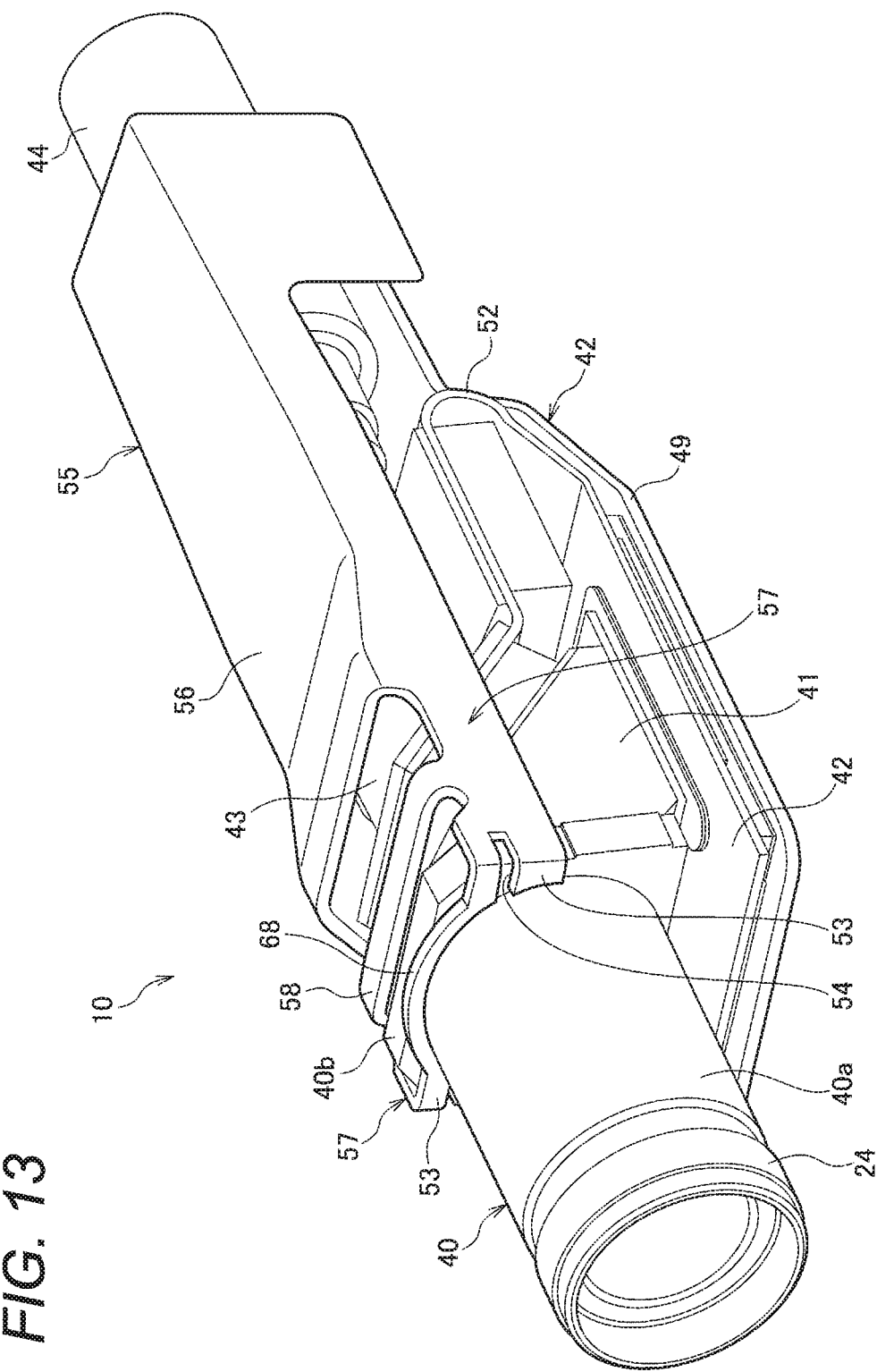
FIG. 13 is a perspective view showing an appearance of a camera module, excluding a housing etc., according to a third embodiment of the invention.

In the second embodiment shown in FIGS. 11 and 12, the link portion 58 is formed at such a position as to stride over the prism 41. FIG. 13 shows another structure in which another link portion 68 which links the nails 53 of the pair of arms 57 is formed at such a position as to stride over the attachment cylinder 40a of the prism holding structure 40. In this case, it is possible to reliably oppose forces that are produced by a pull transmitted by the transmission cable 44 and act on the nails 53 in such directions as to cause them to go away from each other.

As described above, the endoscope disclosed in this specification is equipped with a shooting lens unit having a shooting lens and a housing which holds the shooting lens; a prism on which shooting light coming from the shooting lens shines; a prism holding structure which holds the prism and is attached to one end portion of the housing; an image area sensor which is attached to an exit face of the prism; a circuit board which drives the image area sensor; a transmission cable which is electrically connected to the circuit board; and a cable link structure one end portion of which is fastened to the transmission cable and the other end portion of which is attached to a body structure having the prism holding structure and the housing, wherein the other end portion of the cable link structure is formed with a lock portion which is locked on the body structure, and wherein the lock portion restricts movement of the cable link structure relative to the body portion in two different directions.

One of the two different directions is a direction in which the other end portion of the cable link structure is most prone to be displaced by force received by the one end portion of the cable link structure.

The cable link structure is made of a plate-like member, and the direction in which the other end portion of the cable link structure is most prone to be displaced is a thickness direction of the cable link structure.

The lock portion has a first lock portion which extends in the thickness direction of the cable link structure and a second lock portion which extends perpendicularly from the first lock portion in the thickness direction of the cable link structure, and the body structure is formed with a cut on which the second lock portion in locked.

The lock portion has plural arms which are locked on the body structure at plural positions and a link portion which links the plural arms.

Part of the prism is interposed between the link portion and nails, locked on the body structure, of the plural respective arms.

The nails of the plural arms have respective cuts which are charged with adhesive.

Although the invention has been described above in relation to preferred embodiments and modifications thereof, it will be understood by those skilled in the art that other variations and modifications can be effected in these preferred embodiments without departing from the scope and spirit of the invention.

What is claimed is:
1. An endoscope comprising:
  a shooting lens unit having a shooting lens and a housing which holds the shooting lens;
  a prism on which shooting light coming from the shooting lens shines;

a prism holding structure which holds the prism and is attached to one end portion of the housing;

an image area sensor which is attached to an exit face of the prism;

a circuit board which drives the image area sensor;

a transmission cable which is electrically connected to the circuit board; and a cable link structure one end portion of which is fastened to the transmission cable and other end portion of which is attached to a body structure having the prism holding structure and the housing, wherein:

the other end portion of the cable link structure is formed with a lock portion which is locked on the body structure; and the lock portion restricts movement of the cable link structure relative to the body portion in two different directions, wherein the lock portion has a first lock portion which extends in a thickness direction of the cable link structure and a second lock portion which extends perpendicularly from an arc-shaped edge of the first lock portion in a direction perpendicular to the thickness direction of the cable link structure.

2. The endoscope according to claim 1, wherein:

one of the two different directions is a direction in which the other end portion of the cable link structure is most prone to be displaced by force received by the one end portion of the cable link structure.

3. The endoscope according to claim 2, wherein:

the cable link structure is made of a plate-like member; and the direction in which the other end portion of the cable link structure is most prone to be displaced is the thickness direction of the cable link structure.

4. The endoscope according to claim 2, wherein the lock portion has plural arms which are locked on the body structure at plural positions and a link portion which links the plural arms.

5. The endoscope according to claim 4, wherein part of the prism is interposed between the link portion and nails, locked on the body structure, of the plural respective arms.

6. The endoscope according to claim 4, wherein the nails of the plural arms have respective cuts which are charged with adhesive.

7. The endoscope according to claim 5, wherein the nails of the plural anus have respective cuts which are charged with adhesive.

8. The endoscope according to claim 1, wherein:

the body structure is formed with a cut on which the second lock portion is locked.

9. The endoscope according to claim 1, wherein the lock portion has plural arms which are locked on the body structure at plural positions and a link portion which links the plural arms.

10. The endoscope according to claim 9, wherein part of the prism is interposed between the link portion and nails, locked on the body structure, of the plural respective arms.

11. The endoscope according to claim 10, wherein the nails of the plural arms have respective cuts which are charged with adhesive.

12. The endoscope according to claim 9, wherein the nails of the plural arms have respective cuts which are charged with adhesive.

* * * * *